United States Patent [19]

Tomiyama et al.

[11] Patent Number: 4,978,674
[45] Date of Patent: Dec. 18, 1990

[54] DAIMINE DERIVATIVES, AND METHOD OF MANUFACTURING THE SAME

[75] Inventors: Tsuyoshi Tomiyama; Akira Tomiyama, both of Sakaki; Shuichi Wakabayshi, Koushoku; Hironao Sajiki, Sakaki; Junko Sekiguchi, Ueda, all of Japan

[73] Assignee: Kotobuki Seiyaku Co. Ltd., Nagano, Japan

[21] Appl. No.: 389,050

[22] Filed: Aug. 2, 1989

[30] Foreign Application Priority Data

Sep. 21, 1988 [JP] Japan .................. 63-236885

[51] Int. Cl.$^5$ .................. A61K 31/38; C07D 333/32
[52] U.S. Cl. .................. 514/445; 514/447; 549/64; 549/65; 549/68
[58] Field of Search .................. 549/64, 65, 68, 74; 514/445, 447

[56] References Cited

U.S. PATENT DOCUMENTS

| | | | |
|---|---|---|---|
| 4,482,718 | 11/1984 | Chekroun et al. | 549/68 |
| 4,871,761 | 10/1989 | Wollweber et al. | 549/65 |
| 4,874,876 | 10/1989 | O'Reilly et al. | 549/74 |

FOREIGN PATENT DOCUMENTS 597597  5/1960  Canada .................. 549/74

Primary Examiner—Alan Siegel
Attorney, Agent, or Firm—Emmanuel J. Lobato; Robert E. Burns

[57] ABSTRACT

New antiarrythmic diamines are disclosed. pa These new compounds are represented by the following general formula:

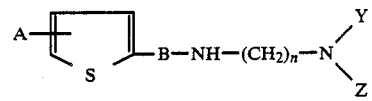

wherein:
A is $NO_2$, $RSO_2NH$ or $RSO_2$, wherein R represents a lower alkyl group.
B is $>CH_2$ or $>C=O$,
Y is a lower alkyl group,
Z is a lower alkyl or benzyl group,
n is an integer 2 or 3.

The compounds of the present invention are useful as antiarrhythmic agents.

9 Claims, No Drawings

DAIMINE DERIVATIVES, AND METHOD OF MANUFACTURING THE SAME

BACKGROUND OF THE INVENTION

This invention relates to new diamine derivatives, therapeutic compositions containing these derivatives and the method of manufacturing the same.

SUMMARY OF THE INVENTION

The principal object of the present invention is the provision of novel compounds having advantageous pharmaceutical properties.

Another object of the present invention is the provision of pharmaceutical compositions useful as antiarrhythmic agents.

Still another object of the present invention is the provision of new diamine derivatives and a method for the manufacture thereof.

These and other objects of the invention will become apparent from the description that follows hereinafter.

DETAILED DESCRIPTION OF THE INVENTION

This invention relates to new diamine derivatives and a method of their synthesis and use as potent antiarrhythmic agents.

Antiarrhythmic agents are classified into 1,2,3 and 4 of the classification of Vaughan Williams, E. M. (Classification of antiarrhythmic drugs.

Pharmacol. Ther. (B), 1, 115–138, (1975). At present, antiarrhythmic agents of class 1, class 2 and class 4 are used for arrhythmia.

Developments of class 3 antiarrhythmics are desired and class 3 antiarrhytymic agents are defined to prolong an effective refractory period of cardiac action potential. Amiodarone is generally known an antiarrhythmic of class 3, but has an abnormal half-life for 50 days and is known to possess lung toxicity (R. W. Kreeger et al.; May. Clin. Pros., 62, 1033 (1988).

Developments of class 3 antiarrhythmics that have none of the deffects mentioned above are demanded.

This invention, under these circumstance, has been made after research of useful compounds for antiarrhythmics.

The compounds of this invention have the following general formula (1):

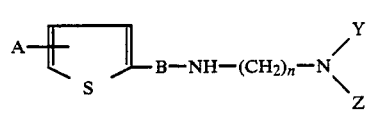
(1)

wherein:
A is NO$_2$, RSO$_2$NH or RSO$_2$, wherein
  R represents a lower alkyl group.
B is >CH$_2$ or >C=O,
Y is a lower alkyl group,
Z is a lower alkyl or benzyl group and
n is an integer 2 or 3.
including pharmaceutically acceptable acid-addition salts thereof.

The term "lower alkyl" as used in this specification designates straight-chain or branched alkyl groups which contain from 1 to 4 carbon atoms.

The compounds of the general formula (1):

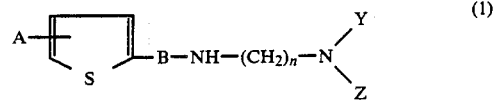
(1)

wherein:
A, n, Y and Z are same as mentioned above,
B is >C=O.
can be prepared by reacting a compound of the general formula (2):

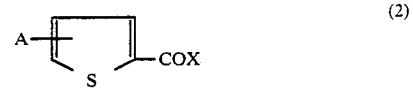
(2)

wherein:
A is same as mentioned above and
X is OH, a lower alkyloxy group or halogen atom
with a compound of the general formula (3):

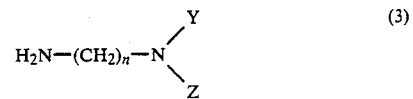
(3)

wherein:
n, N, Y and Z are same as mentioned above,
Alternatively, the compound of the general formula (1):

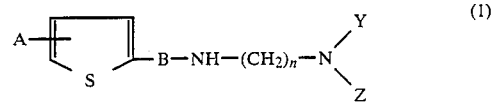
(1)

wherein:
A, n, Y and Z are same as mentioned above,
B is >CH$_2$.
can be obtained by reacting a compound of the general formula (4):

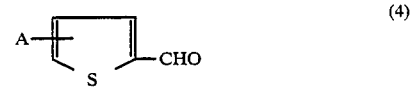
(4)

wherein:
A is same as mentioned above.
with a compound of the general formula (3):

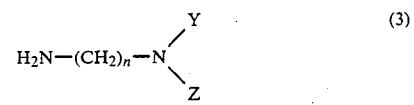
(3)

wherein:
n, Y and Z are same as mentioned above.
in the presence of a reducing agent.

As X is OH in the general formula (2), the reaction of compound of the formula (2) and a compound of the formula (3) can be carried out in the presence of condensing agents such as dicyclohexylcarbodiimide (DCC), diphenylphosphorylazide (DPPA) orcarbonyldiimidazole (CDI).

As the solvent used in this reaction, an aprotic solvent, dimethylformamide (DMF), tetrahydrofuran (THF) and benzene are mentioned and the reaction is carried out at room temperature.

X being a lower alkyloxy group, the reaction of a compound of the formula (2) and a compound of the formula (3) can be carried out by heating in a solvent such as benzene, toluene and xylene. In some cases, the reaction proceeds without a solvent.

As X is a halogen atom in the general formula (2), the reaction of a compound of the formula (2) and a compound of the formula (3) can be carried out in a solvent such as water, acetone and benzene. Although the reaction may proceed without a base, yet its presence is still desirable. As the base required in this reaction, compounds such as alkali metal-hydroxides, amines and the compound of the formula (3) are employed. The reaction proceeds at room temperature or under cooling conditions.

The reaction of a compound of the formula (4) and a compound of the formula (3) requires a reducing agent such a hydride compound as sodium borohydride ($NaBH_4$), and sodium cyanoborohydride ($NaBH_3CN$). Alcoholic solvents are employed in this reaction and the reaction proceeds at room temperature or by heating. The purification of compounds thus obtained is carried out by general methods such as column chromatography and recrystalization.

Some compounds related to the general formula (1) are examplified as follows.

(1) N-(4-Methanesulfonylamino-2-thienoyl), N'-dimethylethylenediamine.HCl (Compound 1)
(2) N-(4-Methanesulfonylamino-2-thienoyl), N'-dimethylethylenediamine (Compound 2)
(3) N-(5-Methanesulfonylamino-2-thienoyl), N'-dimethylethylenediamine.HCl (Compound 3)
(4) N-(4-Methanesulfonylamino-2-thienoyl), N'-diisopropylethylenediamine.HCl (Compound 4)
(5) N-(4-Methanesulfonylamino-2-thienoyl), N'-methyl, N'-benzylethylenediamine . HCl (Compound 5)
(6) N-(4-Nitro-2-thienoyl), N'-dimethylethylenediamine.HCl (Compound 6)
(7) N-(4-Nitro-2-thienoyl), N'-diethylethylenediamine.HCl (Compound 7)
(8) N-(4-Nitro-2-thienoyl), N'-diisopropylethylenediamine.HCl (Compound 8)
(9) N-(4-Nitro-2-thienoyl), N'-methyl, N'-benzylethylenediamine.HCl (Compound 9)
(10) N-(4-Methanesulfonylamino-2-thienoyl), N'-diethylpropylenediamine.HCl (Compound 10)
(11) N-(4-Nitro-2-thienoyl), N'-diethylpropylenediamine.HCl (Compound 11)
(12) N-(5-Nitro-2-thienoyl), N'-diethylethylenediamine.HCl (Compound 12)
(13) N-(4-Methanesulfonyl-2-thienoyl), N'-diethylethylenediamine.HCl (Compound 13)
(14) N-(4-Methanesulfonylaminothiophene-2-yl)methyl, N'-diethylethylenediamine.2HCl (Compound 14)
(15) N-(4-Nitrothiophene-2-yl)methyl, N'-diethylethylenediamine.HCl (Compound 15)
(16) N-(4-Methanesulfonylaminothiophene-2-yl)methyl, N'-diethylpropylenediamine.HCl (Compound 16).

The compounds of the general formula (1) thus obtained can be applied as free base or pharmacologically acceptable acid-addition salts such as hydrochloride, sulfate and fumarate.

The compounds of the invention have an antiarrhythmic effect which will be explained later. They can be administered orally or parenterally. An effective dosage of the compound is from 10 mg to 500 mg a day for adults, though it may be adjusted depending on age and symptoms.

Pharmaceutical, pharmacological and experimental examples of the compounds of this invention are as follows.

(PHARMACEUTICAL EXAMPLE 1)

Ingredients:

| | |
|---|---|
| Compound 2 | 50 mg |
| Lactose | 40 mg |
| Starch | 57 mg |
| Methylcellulose | 3 mg |

The ingredients were mixed and made into granules by a conventional method.

(PHARMACEUTICAL EXAMPLE 2)

Ingredients:

| | |
|---|---|
| Compound 11 | 30 mg |
| Lactose | 30 mg |
| Starch | 45 mg |
| Methylcellulose | 3 mg |
| Magnesium Stearate | 2 mg |

The ingredients were mixed and compressed to give tablets in the usual way.

[PHARMACOLOGICAL EXAMPLE]

Prolongation activities of right ventricular refractory period.

Measurements of transmembrane action potential were carried out according to the method of Kodama et al. (J. Cardiovasc. Pharmacol. 7:1013–1019, 1985) Papillary muscles, 2 to 4 mm in length and 1~2 mm in diameter, were isolated from right ventricle of guinea pigs weighing 250 to 350 g. The preparation was superfused with Krebs-Ringer solution at 34° C. and stimulated via a pair of Ag-AgCl wire electrodes.

Transmembrane potential was recorded through two glass microelectrodes filled with 3 M KCl (resistance, 30~40 KΩ). Action potential and their first derivative were displayed simultaneously on a oscilloscope and were photographeled. Solutions of the test compounds, ranging in concentration from $10^{-6}$ to $10^{-4}$ M. were superfused for 30 minutes, individually. Action potential duration at 95% repolarization ($APD_{95}$) was measured and the concentration which prolonged $APD_{95}$ by 20% was calculated. The results are illustrated in Table 1.

TABLE 1

| Compound | Concentration of 20% increase in $ADP_{95}$ |
|---|---|
| 2 | $9.6 \times 10^{-6}$ |
| 4 | $1.9 \times 10^{-5}$ |
| 5 | $3.0 \times 10^{-5}$ |
| 7 | $2.3 \times 10^{-6}$ |
| 9 | $9.8 \times 10^{-6}$ |
| 10 | $5.5 \times 10^{-5}$ |
| 11 | $1.0 \times 10^{-6}$ |
| 14 | $3.9 \times 10^{-6}$ |
| 15 | $1.5 \times 10^{-5}$ |

| TABLE 1-continued | |
|---|---|
| Compound | Concentration of 20% increase in ADP$_{95}$ |
| 16 | $8.2 \times 10^{-6}$ |

EXAMPLE 1

N-(4-Methanesulfonylamino-2-thienoyl), N'-dimethylethylenediamine.HCl (Compound 1)

(a) A mixture of 1.0 g. of methyl 4-methanesulfonylamino-2-thiophene carboxyl ate and 0.41 g. of N,N-dimethylethylenediamine was heated at 70° C. under argon atmosphere and stirred for 20 hours. After cooling, the mixture was chromatographed on silica gel, eluted with chloroform-methanol (10:1). 0.45 g. of N-(4-methanesulfonylamino-2-thienoyl), N'-dimethylethylenediamine was obtained.

(b) To a solution of 0.45 g. of N-(4-methanesulfonylamino-2-thienoyl), N'-dimethylethylenediamine, obtained in (a), in 20 ml. of methanol, 1.0 ml. of ca.13% HCl-MeOH sol. was added. Solvent was removed in vacuo, and then the residue was washed with ether. 0.46 g. of N-(4-methanesulfonylamino-2-thienoyl), N'-dimethylethylenediamine. HCl was obtained. m.p.: 43° C. (decomp.). M.S.(m/e): 291 (M+-HCl), 204, 168, 125, 97, 71, 58 (B.P.). I.R.(cm$^{-1}$): 3418, 1635, 1563, 1530, 1359, 1149, 987, 516.

EXAMPLE 2

N-(4-Nitro-2-thienoyl), N'-diethylethylenediamine. HCl (Compound 7)

(a) A mixture of 2.80 g. of 4-Nitro-2-thiophene carboxylic acid and 1.88 g. of N,N-diethylenediamine was cooled with an ice bath. Dicyclohexylcarbodiimide 3.34 g. was added to the mixture and the mixture was stirred for 1 hr. at ambient temperature. Resulting dicyclohexylurea was removed by filtration, filtrate was concentrated. The residue was subjected to silica gel column-chromatography, and, eluted with ether, to give 2.40 g. of N-(4-Nitro-2-thienoyl), N'-diethylethylenediamine.

(b) The compound obtained in (a) was converted to a HCl salt in the usual manner and 2.45 g. of N-(4-Nitro-2-thienoyl), N'-diethylaminoethylene diamine HCL was obtained. m.p.: 174°~175° C. M.S. (m/e): 271 (M+-HCl), 199, 156, 110, 82 (B.P.). I.R.(cm$^{-1}$): 2650, 1662, 1539, 1338.

EXAMPLE 3

N-(4-Methanesulfonylaminothiophene-2-yl)methyl, N'-diethylethylenediamine.2HCl (Compound 14)

(a) A mixture of 1.5 g. of 4-Methanesulfonylamino-2-thiophenealdehyde and 0.93 g. of N,N-diethylethylenediamine in methanol (60 ml) was stirred at room temperature for 20 min. Sodium borohydride (NaBH$_4$) was added to the solution and then stirred at room temperature for 10 min. The reaction mixture was neutralized (about pH 9) by c.HCl, the solvent was removed under reduced pressure. The residue was purified by silica gel column chromatography, and eluted with chloroform-methanol (4:1) to give 1.69 g of N-(4-Methanesulfonylaminothiophene-2-yl)methyl, N'-diethylethylenediamine.

(b) The compound obtained in (a) was converted to a HCl salt as in the same manner as that described in EXAMPLE 1 (b) to give 0.45 g. of N-(4-Methanesulfonylaminothiophene-2-yl)methyl, N'-diethylethylene diamine 2HCl.

EXAMPLE 2~16

The compounds from No. 2 to No. 13 were obtained in the same manner as EXAMPLE 1 and compound No. 15 and No. 16 were obtained according to the same procedure as that of EXAMPLE 3.

TABLE 2

$$A\!-\!\!\underset{S}{\boxed{\phantom{xx}}}\!-\!B\!-\!NH\!-\!(CH_2)_n\!-\!N\!\!<\!\!\genfrac{}{}{0pt}{}{Y}{Z}$$

| Compound | A | B | n | Y | Z | m.p.(°C.) | M.S.(m/e) |
|---|---|---|---|---|---|---|---|
| 2 | 4-CH$_3$SO$_2$NH— | \C=O/ | 2 | Et | Et | Oil | 319(M+) |
| 3 | 5-CH$_3$SO$_2$NH— | \C=O/ | 2 | Et | Et | 196-7 | 319(M+-HCl) |
| 4 | 4-CH$_3$SO$_2$NH— | \C=O/ | 2 | iso-Pro | iso-Pro | 61-2 | 347(M+-HCl) |
| 5 | 4-CH$_3$SO$_2$NH— | \C=O/ | 2 | Me | CH$_2$Ph | 78 (decomp.) | 367(M+-HCl |
| 6 | 4-NO$_2$ | \C=O/ | 2 | Me | Me | 204-6 | 243(M+-HCl) |

TABLE 2-continued $$A\underset{S}{\underset{|}{\overline{\phantom{xx}}}}B-NH-(CH_2)_n-N\underset{Z}{\overset{Y}{\diagdown}}$$

| Compound | A | B | n | Y | Z | m.p.(°C.) | M.S.($m/e$) |
|---|---|---|---|---|---|---|---|
| 8 | 4-NO$_2$ | >C=O | 2 | iso-Pro | iso-Pro | 190–3 | 299(M$^+$-HCl) |
| 9 | 4-NO$_2$ | >C=O | 2 | Me | CH$_2$Ph | 189–192 | 319(M$^+$-HCl) |
| 10 | 4-CH$_3$SO$_2$NH— | >C=O | 3 | Et | Et | 48 (decomp.) | 331(M$^+$-HCl) |
| 11 | 4-NO$_2$ | >C=O | 3 | Et | Et | 150–3 | 285(M$^+$-HCl) |
| 12 | 5-NO$_2$ | >C=O | 2 | Et | Et | 196–7 (decomp.) | 271(M$^+$-HCl) |
| 13 | 4-CH$_3$SO$_2$— | >C=O | 2 | Et | Et | 181–3 | 304(M$^+$-HCl) |
| 15 | 4-NO$_2$ | >CH$_2$ | 2 | Et | Et | 105–6 | 257(M$^+$-HCl) |
| 16 | 4-CH$_3$SO$_2$NH— | >CH$_2$ | 3 | Et | Et | Oil | 319(M$^+$-2HCl) |

What we claim is:

1. A compound of the formula:

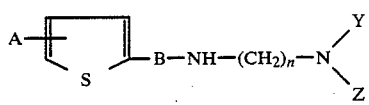

wherein:
A is —NO$_2$, —SO$_2$—R or —NH—SO$_2$—R wherein R represents a lower alkyl group;
B is >CH$_2$ or >CO;
Y is a lower alkyl group;
Z is a lower alkyl or benzyl group and n represents 2 or 3, and
pharmaceutically acceptable acid addition salts thereof.

2. A compound according to claim 1 wherein A is a nitro and B represents a carbonyl group.

3. A compound according to claim 1 wherein A is a lower alkyl sulfonylamino group and B represents a carbonyl group.

4. A compound according to claim 1 wherein A is a lower alkyl sulfonyl group.

5. A compound according to claim 1 wherein A is a lower alkyl sulfonylamino group and B represents >CH$_2$.

6. A compound according to claim 1 wherein A is a nitro group and B represents >CH$_2$.

7. A compound according to claim 1 wherein A is CH$_3$SO$_2$NH- and B is >CO or >CH$_2$.

8. An antiarrhythmic composition containing such an amount of a compound as defined in claim 1, as is effective to inhibit arrhythmia, in combination with a pharmaceutically acceptable carrier.

9. A method for treating arrhythmia, comprising administering a compound as defined in claim 1 effective as an antiarrhythmic agent.

* * * * *